(12) United States Patent
Sakuta

(10) Patent No.: US 9,784,700 B2
(45) Date of Patent: Oct. 10, 2017

(54) X-RAY ANALYZER

(71) Applicant: Hitachi High-Tech Science Corporation, Minato-ku, Tokyo (JP)

(72) Inventor: Masahiro Sakuta, Tokyo (JP)

(73) Assignee: Hitachi High-Tech Science Corporation, Minato-ku, Tokyo (JP)

( * ) Notice: Subject to any disclaimer, the term of this patent is extended or adjusted under 35 U.S.C. 154(b) by 286 days.

(21) Appl. No.: 14/611,668

(22) Filed: Feb. 2, 2015

(65) Prior Publication Data

US 2015/0268179 A1 Sep. 24, 2015

(30) Foreign Application Priority Data

Mar. 20, 2014 (JP) .................................. 2014-058388

(51) Int. Cl.
*G01N 23/22* (2006.01)
*G06F 1/16* (2006.01)
(Continued)

(52) U.S. Cl.
CPC ......... *G01N 23/223* (2013.01); *G06F 1/1692* (2013.01); *G06F 3/017* (2013.01);
(Continued)

(58) Field of Classification Search
CPC .... G01N 21/00; G01N 21/01; G01N 21/0137; G01N 21/0181; G01N 21/62–21/64; G01N 21/645; G01N 21/6456; G01N 23/00; G01N 23/22; G01N 23/2206; G01N 23/223; G01N 35/00584; G01N 37/00; G01N 2201/00; G01N 2201/102; G01N 2201/103; G01N 2201/125; G01N 2223/00; G01N 2223/07; G01N 2223/071; G01N 2223/076; G01N 2223/10; G01N 2223/101; G01N 2223/1016; G01N 2223/30;
(Continued)

(56) References Cited

U.S. PATENT DOCUMENTS 3,413,067 A * 11/1968 Froio ................. G02B 23/2423
359/837
5,037,194 A * 8/1991 Kohayakawa ........... A61B 3/12
351/206
(Continued)

FOREIGN PATENT DOCUMENTS

JP 2000-106119 A 4/2000

*Primary Examiner* — Anastasia Midkiff
(74) *Attorney, Agent, or Firm* — Banner & Witcoff, Ltd.

(57) ABSTRACT

A fluorescent X-ray analyzer includes a sample stage, an X-ray source that irradiates a sample with primary X-rays, a detector that detects secondary X-rays generated from the sample, a position adjustment mechanism that adjusts relative positions of the sample stage and the primary X-rays, an observation mechanism that obtains an observation image of the sample, and a computer having a display unit and an input unit. The computer has a function of, in response to a pointer being moved from a central region of the observation screen to a certain position by dragging the input unit while maintaining a state in which an input element of the input unit is held, moving the sample stage in a movement direction and at a movement speed corresponding to a direction and a distance of the certain position relative to the central region.

4 Claims, 3 Drawing Sheets

(51) Int. Cl.
*G06F 3/033* (2013.01)
*G06F 3/048* (2013.01)
*G01N 23/223* (2006.01)
*G06F 3/0354* (2013.01)
*G06F 3/01* (2006.01)
*G06F 3/041* (2006.01)
*G06F 3/0484* (2013.01)

(52) U.S. Cl.
CPC ...... *G06F 3/03547* (2013.01); *G06F 3/03548* (2013.01); *G06F 3/0416* (2013.01); *G06F 3/0484* (2013.01); *G06F 3/04842* (2013.01); *G06F 3/04845* (2013.01); *G06F 3/04847* (2013.01); *G01N 2201/103* (2013.01); *G01N 2201/125* (2013.01); *G01N 2223/076* (2013.01); *G01N 2223/304* (2013.01); *G01N 2223/306* (2013.01); *G01N 2223/408* (2013.01); *G01N 2223/427* (2013.01); *G06F 2203/04104* (2013.01)

(58) Field of Classification Search
CPC ....... G01N 2223/304; G01N 2223/306; G01N 2223/33; G01N 2223/3307; G01N 2223/3308; G01N 2223/40; G01N 2223/408; G01N 2223/421; G01N 2223/427; G06F 1/00; G06F 1/16; G06F 1/1601; G06F 1/1643; G06F 1/169; G06F 1/1692; G06F 3/00; G06F 3/01; G06F 3/016; G06F 3/017; G06F 3/033; G06F 3/03547; G06F 3/03548; G06F 3/0416; G06F 3/048; G06F 3/0484; G06F 3/04841; G06F 3/04845; G06F 3/04847; G06F 3/0486–3/0488; G06F 3/14; G06F 2203/04104; G06F 3/04842

See application file for complete search history.

(56) References Cited

U.S. PATENT DOCUMENTS

| 5,469,254 | A | * | 11/1995 | Konomura | G02B 23/2476 348/65 |
|---|---|---|---|---|---|
| 2005/0028482 | A1 | * | 2/2005 | Cable | A61B 5/0059 52/749.1 |
| 2009/0015663 | A1 | * | 1/2009 | Doettling | F16P 3/14 348/46 |
| 2010/0149489 | A1 | * | 6/2010 | Kikawa | A61B 3/102 351/206 |
| 2010/0246935 | A1 | * | 9/2010 | Hallock | G01N 23/04 382/146 |
| 2011/0015504 | A1 | * | 1/2011 | Yoo | A61B 5/0002 600/301 |

* cited by examiner

X-RAY ANALYZER

This application claims priority from Japanese Patent Application No. 2014-058388 filed on Mar. 20, 2014, the entire subject matter of which is incorporated herein by reference.

BACKGROUND

1. Technical Field

The present invention relates to an X-ray analyzer, such as a fluorescent X-ray analyzer, which can detect a toxic substance or the like, and is thus used to screen a product or measure a film thickness of plating.

2. Description of the Related Art

Fluorescent X-ray analysis is a method in which a sample is irradiated with X-rays emitted from an X-ray source, and fluorescent X-rays which are characteristic X-rays radiated from the sample are detected by an X-ray detector so that a spectrum is acquired on the basis of energy thereof, thereby performing qualitative or quantitative analysis or measuring a film thickness of the sample. Such fluorescent X-ray analysis allows the sample to be rapidly analyzed in a nondestructive manner and is thus widely used for process and quality management and the like. In recent years, high accuracy and high sensitivity have been achieved in the fluorescent X-ray analysis, and thus a trace measurement can be performed. As a particular result, the fluorescent X-ray analysis is expected to be widespread as an analysis method for detecting toxic substances contained in a material, a complex electronic component, or the like.

In an apparatus which performs such fluorescent X-ray analysis, generally, in order to determine an X-ray irradiation portion (measurement portion), a sample observation image obtained by a CCD camera is displayed on a display screen, and an operation of moving a sample stage is performed by using a pointing device such as a mouse or a touch panel on the screen. In the fluorescent X-ray analyzer, driving is generally performed on three-axis coordinates of XY axes in the horizontal direction and a Z axis in the vertical direction. The XY axes are frequently operated for positioning.

Recently, in order to measure a component or a substrate pattern which has been micronized, an X-ray beam diameter of the apparatus and a visual field of a camera tend to be decreased. Thus, the entire size of the sample stage is relatively increased. For this reason, an improvement of an operation system has been explored in order to rapidly determine a minute position in the wide sample stage.

In the related art, for example, JP-A-2000-106119 discloses a charged particle beam scanning type device in which a plurality of functions are realized by a mouse click and are used through single-clicking and double-clicking. Thus, operability can be improved by reducing labor for moving a mouse pointer to a region of a toolbar button or the like.

The above-described related art, for example, describes: an operation (XY movement operation) in which a button on a screen periphery is pressed with the mouse, and, only while the button is pressed, a sample stage is moved in a direction thereof; an operation (central movement operation) in which the sample stage is driven so that a point on the screen which is clicked with the mouse or the like as a measurement target is moved to a screen center; and an operation (enlargement operation) in which magnification of the camera is increased in a case where a minute position is focused on. Among the operations, such as the XY movement operation, an operation is generally used in which a movement speed of the sample stage is switched with a toolbar button.

The related art has the following problems.

In the related art, an operation is generally used in which a movement speed of the sample stage is switched with a toolbar button in the XY movement operation. However, a procedure for fine movement to a point spaced apart from a present point includes the following. First, rough positioning is performed while switching a movement speed in the XY movement operation, and while a target point is moved within a visual field of the camera. Second, fine positioning is performed in the central movement operation. Here, in a case where finer positioning is necessary, positioning is easily performed by changing the magnification in the enlargement operation. However, a mouse cursor is required to be moved a lot on the screen during the switching of a movement speed, the XY movement operation, and the central movement operation. Thus, fine position requires a significant amount of time. In addition, in the enlargement operation, a mouse pointer (cursor) is required to be moved to the magnification changing button or the like of the toolbar, and thus operability is also reduced.

SUMMARY

Therefore, illustrative aspects of the present invention provide an X-ray analyzer capable of improving operability for performing fine positioning of a wide sample stage.

According to a first illustrative aspect of the present invention, an X-ray analyzer may include: a sample stage on which a sample is placed; an X-ray source configured to irradiate the sample with primary X-rays; a detector configured to detect secondary X-rays generated from the sample irradiated with the primary X-rays; a position adjustment mechanism configured to adjust relative positions of the sample stage and the primary X-rays; an observation mechanism for obtaining an observation image of the sample on the sample stage; and a computer configured to control the position adjustment mechanism, wherein the computer comprise: a display unit that displays the sample observation image on an observation screen; and an input unit for inputting a position on a screen of the display unit with a pointer and for performing a drag-and-drop operation, wherein the computer has a function of, in response to the pointer being moved from inside a central region of the observation screen to a certain position out of the central region by the input unit being dragged while keeping a button of the input unit in a held state, driving the position adjustment mechanism in a movement direction and at a movement speed corresponding to a direction and a distance of the certain position relative to the central region, so as to move the sample stage.

In the X-ray analyzer, when the pointer is operated to be dragged from inside the central region of the observation screen to a certain position outside the central region while the button of the input unit is held, the computer has a function of driving the position adjustment mechanism in a movement direction and at a movement speed corresponding to a direction and a distance of the certain position relative to the central region so as to move the sample stage. Therefore, a movement direction and a movement speed of the sample stage can be set and operated simply by performing a drag-and-drop operation. In other words, a movement direction of the sample stage using the position adjustment mechanism is determined on the basis of a start point of the dragging and a dragging direction, and a movement speed is determined on the basis of a distance between the start point of the dragging and a position to which the pointer is moved while the button of the input unit is in the held state. Thus, a movement speed of the sample stage, which is set with a button outside the observation screen on which a sample observation image is displayed in the related art, can be intuitively indicated by a dragging distance and can also be changed at any time even during scanning in the present invention.

According to a second illustrative aspect of the present invention, in the X-ray analyzer according to the first aspect, the computer may be configured to control the display unit to display, on the observation screen, mesh lines that are formed by a plurality of concentric lines, the diameters of which become larger in stages, and a plurality of radial division lines which extend from the minimum concentric line with the minimum diameter to the maximum concentric line with the maximum diameter in a radial form among the concentric lines. The observation screen is partitioned into a plurality of division regions by the mesh lines, and the central region may be located inside of the minimum concentric line, and the certain position corresponds to one of the plurality of division regions.

In other words, in the X-ray analyzer, the observation screen is partitioned into a plurality of division regions with the mesh lines, the central region is located inside of the minimum concentric line, and the certain position to which the pointer is moved in a holding state corresponds to one of the plurality of division regions. Therefore, a movement direction and a movement speed are determined in stages on the basis of positions of the division regions which are cells partitioned with the mesh lines. In addition, since the observation screen is partitioned with the concentric lines, distances in the vertical direction, the horizontal direction, and the diagonal direction are the same as each other, and thus an operation can be performed in the same operation amount even if the operation is performed in any direction.

According to a third illustrative aspect of the present invention, in the X-ray analyzer according to the first or the second aspect, the input unit may be a mouse for controlling the pointer on the screen of the display unit, the mouse having a rotatable wheel and allowing an input corresponding to a rotation operation of the wheel to be performed, and the computer may have a function of changing display magnification of the sample observation image captured by the observation mechanism in accordance with a rotation direction of the wheel.

In other words, in the X-ray analyzer, when the wheel of the input unit is rotated, the computer has a function of changing display magnification of a sample observation image obtained by the observation mechanism, in accordance with a rotation direction of the wheel. Therefore, a magnification changing button of the toolbar or the like is not required to be pressed, and thus operability can be further improved.

According to a fourth illustrative aspect of the present invention, in the X-ray analyzer according to the first or the second aspect, the input unit may be a touch panel which allows a position to be input through touching of the screen of the display unit, the touch panel allowing an input corresponding to pinch operations including pinch-in and pinch-out to be performed. Additionally, the computer may have a function of changing display magnification of the sample observation image captured by the observation mechanism depending on the pinch-in or the pinch-out operation.

In other words, in the X-ray analyzer, when a pinch operation is performed by using the input unit, the computer has a function of changing display magnification of a sample observation image obtained by the observation mechanism depending on pinch-in or pinch-out, and thus a button of the toolbar or the like is not required to be pressed. Operability can be further improved thereby. Therefore, even in an operation on the touch panel using finger tips which do not have high positioning accuracy, an operation related to the sample stage can be intuitively performed.

According to a fifth illustrative aspect, in the X-ray analyzer according to the first or the second illustrative aspect, the input unit may be configured to receive a sliding operation, and the computer may have a function of, in response to receiving the sliding operation, changing display magnification of the sample observation image captured by the observation mechanism in accordance with a direction of the sliding operation.

The illustrative aspects of the present invention can provide the following advantages.

According to the X-ray analyzer related to the present invention, when the pointer is dragged from inside the central region of the observation screen to a certain position outside the central region in a state where a button of the input unit is held, the computer has a function of driving the position adjustment mechanism in a movement direction and at a movement speed corresponding to a direction of the movement and a distance of the certain position relative to the central region, to move the sample stage. Therefore, a movement direction and a movement speed of the sample stage can be set and operated simply by performing a drag-and-drop operation. Consequently, in the X-ray analyzer, it is possible to easily perform fine positioning in the wide sample stage through a simple operation such as the drag-and-drop operation, thereby improving operability.

In addition, in a case where the XY movement operation is performed as in the related art, it is not necessary to temporarily stop operating the input unit in order to move the pointer to an XY movement button of the toolbar. As such, the XY movement operation can be performed through continuous moving operations of the pointer in a direction in which the pointer is desired to be moved. Similarly, in the case of changing movement speed, it is possible to continuously increase and decrease a speed without having to move to a movement speed adjustment button of the toolbar and without having to stop an operation of the input unit. As described above, according to the present invention, the stage is not decelerated or stopped due to an operation being stopped during observation of a sample, and a direction and a distance in and at which a pointer is desired to be moved can be intuitively indicated on the basis of a dragging distance using the input unit even during scanning. Accordingly, it is possible to considerably improve operability.

DETAILED DESCRIPTION

Hereinafter, the present embodiment of an X-ray analyzer according to the present invention will be described with reference to FIGS. 1 and 2.

Figure 1:
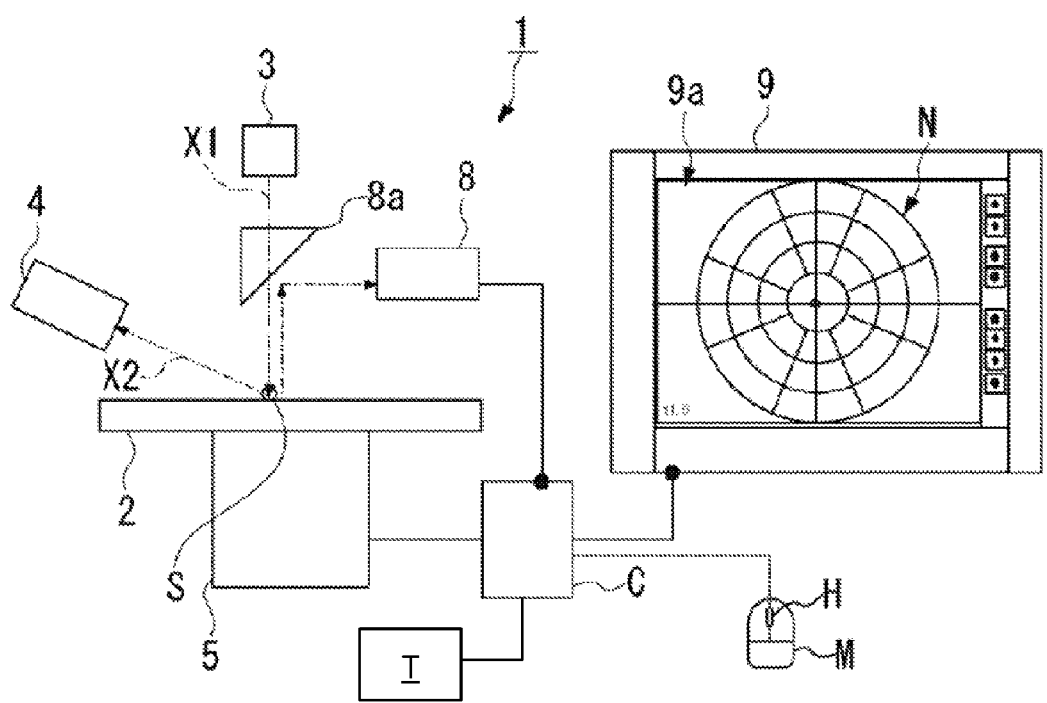
FIG. 1 is a schematic entire configuration diagram illustrating an embodiment of an X-ray analyzer according to the present invention.

An X-ray analyzer 1 of the present embodiment is, for example, a fluorescent X-ray analyzer which detects fluorescent X-rays as secondary X-rays, and, as illustrated in FIG. 1, includes a sample stage 2 on which a sample S is placed, an X-ray source 3 which irradiates the sample S with primary X-rays X1, a detector 4 which detects secondary X-rays X2 generated from the sample S which is irradiated with the primary X-rays X1, a position adjustment mechanism 5 which adjusts relative positions between the sample stage 2 and the primary X-rays X1, an observation mechanism 8 which captures an observation image of the sample on the sample stage 2, and a computer C having a display unit 9 which controls the position adjustment mechanism 5 and displays a sample observation image on an observation screen 9a, and input unit M for inputting a position on a screen of the display unit 9 with a pointer P and for performing a drag-and-drop operation.

Figure 2:
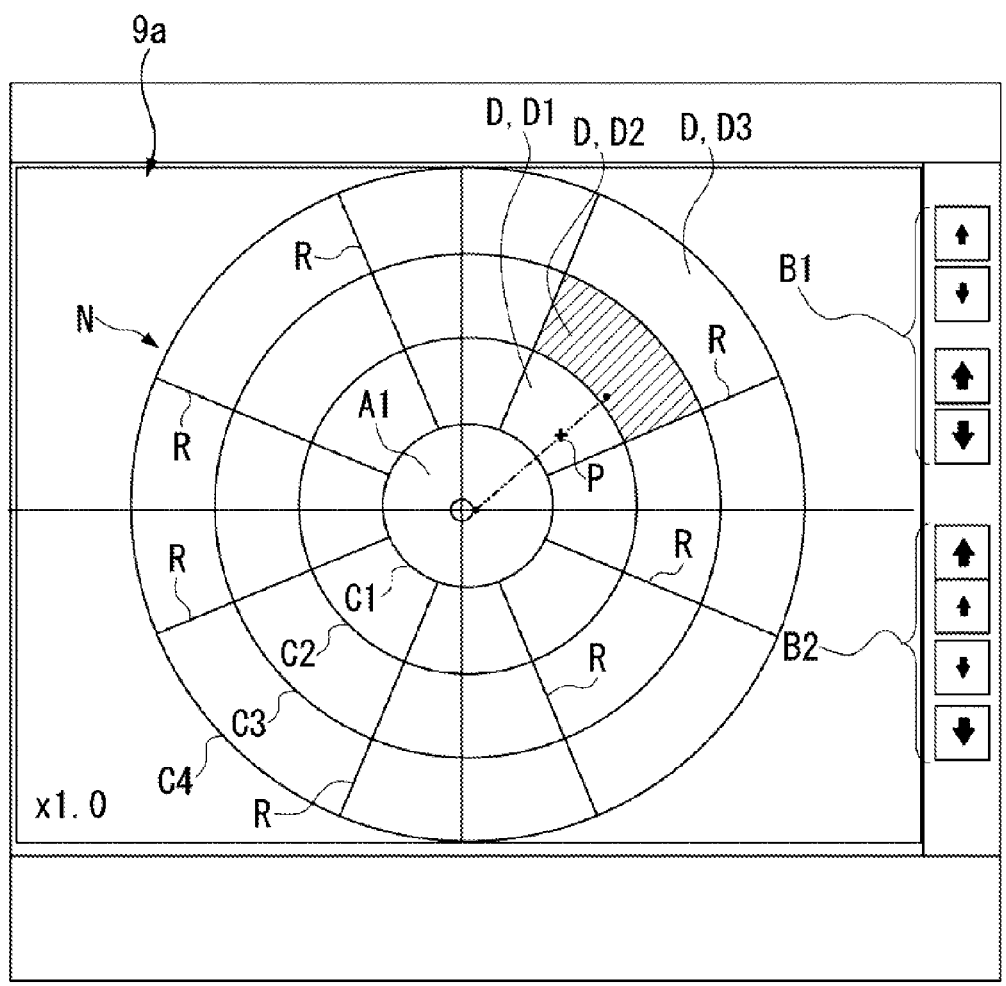
FIG. 2 is a diagram illustrating an image example of a display unit in the present embodiment.

As illustrated in FIG. 2, the computer C has a function of, when the pointer P located inside a central region A1 of the observation screen 9a is moved to a certain position out of the central region A1 by dragging the input unit M with an input element in a held state (e.g., a button being held down), driving the position adjustment mechanism 5 in a movement direction and at a movement speed corresponding to a direction and a distance of the certain position relative to the central region A1, so as to move the sample stage 2. In other words, the computer C controls the position adjustment mechanism 5 on the basis of a software program for realizing the function.

The computer C displays, on the observation screen 9a, mesh lines N formed by a plurality of concentric lines C1 to C4 whose diameters are set to become larger in stages and a plurality of radial division lines R which extend from the minimum concentric line C1 to the maximum concentric line C4 in a radial form among the concentric lines C1 to C4. The observation screen 9a is partitioned into a plurality of division regions D with the mesh lines N, the central region A1 is located inside of the minimum concentric line C1, and the certain position corresponds to one of the plurality of division regions D. In other words, a movement direction and a movement speed are determined in the units of the division regions D, which are cells partitioned by the mesh lines N.

As described above, in the present embodiment, the mesh lines N are formed by the four concentric lines C1 to C4, which are enlarged in diameters at the same intervals, and the eight radial division lines R which radially extend from the center at the same angles. Therefore, a movement speed is divided into three stages based on a dragging direction, and a dragging direction is divided into eight directions. In addition, the mesh lines N are displayed on the observation screen 9a only during a drag-and-drop operation using the input unit M.

The input unit M, which is a mouse as a pointing device, displays the pointer (cursor) P on the screen of the display unit 9, has a rotatable wheel H, and allows an input corresponding to a rotation operation of the wheel H to be performed. In addition, when the wheel H of the input unit M is rotated, the computer C has a function of changing display magnification of a sample observation image captured by the observation mechanism 8, in accordance with a rotation direction of the wheel H.

The observation mechanism 8 is a CCD camera which captures a sample observation image including the sample S on the sample stage 2.

In addition, an optical system 8a is a half mirror or a beam splitter which is disposed on an optical axis of the primary X-rays X1, and transmits the primary X-rays X1 therethrough without change toward the sample stage 2. The optical system 8a also causes a sample observation image to be captured when an optical axis of the observation mechanism 8 is changed toward the sample stage 2.

The computer C is constituted by a CPU and the like, and includes the display unit 9 which can display a sample observation image and an analysis result. In addition, the sample observation image is displayed on the observation screen 9a of the display unit 9 as illustrated in FIG. 1, and a center of the observation screen 9a corresponds to an irradiation position of the primary X-rays X1.

Further, when any position on the observation screen 9a is clicked by using the input unit M, the computer C has a function of moving the sample stage 2 by using the position adjustment mechanism 5 so that the clicked position is moved to the center of the observation screen 9a.

The sample S can be placed on the sample stage 2. The sample stage 2 is disposed on the position adjustment mechanism 5. The position adjustment mechanism 5 is an XY-axis stage and a Z-axis stage, which are controlled by the computer C and can advance and retract the sample stage 2 in XY directions (horizontal direction) and a Z direction (vertical direction).

The X-ray source 3 is an X-ray bulb which can apply the primary X-rays X1. For example, thermal electrons generated from a filament (cathode) of the bulb are accelerated by a voltage applied between the filament (cathode) and a target (anode) and collided with tungsten (W), molybdenum (Mo), and chrome (Cr) of the target. As a result, X-rays are generated and are emitted from a window such as a beryllium foil as the primary X-rays X1. A condensing element (not illustrated) such as a monocapillary, a collimator, or a polycapillary which collects the primary X-rays X1 and irradiates the sample S on the sample stage 2 therewith, is provided on a tip end side of the X-ray source 3.

The detector 4 includes a semiconductor detection element (for example, a silicon (Si) element which is a pin type diode) (not illustrated) provided at an X-ray incidence window, and generates a current pulse corresponding to a single X-ray photon when the X-ray photon is incident thereto. An instantaneous current value of the current pulse is proportional to energy of the incident characteristic X-rays. In addition, the detector 4 is set to convert the current pulse generated by the semiconductor detection element into a voltage pulse which is then amplified and output as a signal.

The X-ray analyzer 1 includes an analyzer (not illustrated) which is connected to the detector 4 and analyzes the signal from the detector 4. The analyzer is a pulse height analyzer (multichannel pulse height analyzer) which obtains a height of the voltage pulse from the signal and generates an energy spectrum.

The computer C has a function of displaying a focus adjustment button B1 of the observation mechanism 8, a Z-axis movement button B2 of the sample stage 2 using the position adjustment mechanism 5, and an XY direction movement button B3 of the sample stage 2 using the position adjustment mechanism 5, on the screen of the display unit 9, along with the observation screen 9a. The focus adjustment button B1 and the Z-axis movement button B2 may be respectively sorted as a low speed adjustment button and a high speed adjustment button. The pointer P is moved onto the focus adjustment button B1 or the Z-axis movement button B2, and, in this state, the button is clicked with the input unit M, so that a focus adjustment of the observation mechanism 8 or a position adjustment of the sample stage 2 can be performed.

In the present embodiment, in a case where a position of the sample stage 2 is adjusted on the observation screen 9a, an operation is differentiated into a clicking operation or a dragging operation using the input unit M. When the clicking operation is performed, as described above, the sample stage 2 is moved by the position adjustment mechanism 5 so that a clicked position is moved to the center of the observation screen 9a.

In addition, when the dragging operation is performed inside the central region A1, the computer C displays the mesh lines N on the observation screen 9a. In this state, the pointer P is moved on the observation screen 9a in a state in which the dragging operation is maintained with the input unit M, and the sample stage 2 is moved by the position adjustment mechanism 5 in the movement direction. In other words, in a case where a start point of the dragging operation is inside the central region A1, the position adjustment mechanism 5 is driven, and a direction in which the sample stage 2 is moved is determined on the basis of the dragging direction (a direction of the pointer P which is moved in a state in which the dragging operation is maintained). A trajectory of the pointer P in a state in which the dragging operation is maintained is displayed as a line on the observation screen 9a.

In addition, a movement speed of the sample stage 2 is determined on the basis of a distance of the pointer P moved in the state in which an input element of the input unit is held. In other words, a movement speed is set to become higher as a distance from the central region A1 to the pointer P is lengthened. For example, in FIG. 2, a movement speed of the sample stage 2 is set to be higher in a case where the pointer P is moved from the central region A1 to the division region D3 than in a case where the pointer P is moved from the central region A1 to the division region D1, even in the same direction.

Next, when the pointer P is moved to any one of the division regions D and is operated to be dropped with the input unit M, the computer C stops the movement of the sample stage 2 by using the position adjustment mechanism 5 and erases the display of the mesh lines N on the observation screen 9a.

Therefore, the X-ray analyzer 1 has an operation system in which the movement of the sample stage 2 is performed only on the observation screen 9a.

In addition, in the present embodiment, on the basis of restrictions of hardware of the apparatus, movement directions and movement speeds are set to be the same even if the pointer P is moved to any position in a single division region D, and thus movement directions and movement speeds are set in stages as a whole. However, a movement direction and a movement speed may be set to be continuously determined according to a direction and a distance of a position of the pointer P in a region other than the central region A1, to which the pointer P is moved, relative to a start point of a dragging operation inside the central region A1, regardless of the division regions D.

As described above, in the X-ray analyzer 1 of the present embodiment, when the pointer P is operated to be dragged from inside the central region A1 of the observation screen 9a to a certain position outside the central region A1 in a state in which an input element of the input unit M is held, the computer C has a function of driving the position adjustment mechanism 5 in a movement direction and at a movement speed corresponding to a direction and a distance of the certain position relative to the central region A1 so as to move the sample stage 2. Therefore, a movement direction and a movement speed of the sample stage 2 can be set and operated simply by performing a drag-and-drop operation.

Thus, a movement speed of the sample stage 2, which is set with a button outside the observation screen 9a on which a sample observation image is displayed in the related art, can be intuitively indicated by a dragging distance and can also be changed at any time even during scanning.

In addition, the observation screen 9a is partitioned into the plurality of division regions D with the mesh lines N, the central region A1 is located inside the minimum concentric line C1, and any position to which the pointer P is moved in a holding state (e.g., a state in which an input element of the input unit M is held) corresponds to one of the plurality of division regions D. Thus, a movement direction and a movement speed can be determined in stages according to positions of the division regions D which are partitioned with the mesh lines N. Further, since the observation screen 9a is partitioned with the concentric lines C1 to C4, distances in the vertical direction, the horizontal direction, and the diagonal direction are the same as each other, and thus an operation can be performed in the same operation amount even if the operation is performed in any direction.

Still further, when the wheel H of the input unit M is rotated, the computer C has a function of changing display magnification of a sample observation image captured by the observation mechanism 8, in accordance with a rotation direction of the wheel H. Therefore, a magnification changing button of the toolbar or the like is not required to be pressed, and thus operability can be further improved.

In addition, the technical scope of the present invention is not limited to the above-described embodiment and may have various modifications within the scope which does not depart from the spirit of the present invention.

For example, the above-described embodiment is applied to an energy distribution type X-ray analyzer which measures energy and intensity of X-rays with the pulse height analyzer, but is applicable to a wavelength distribution type X-ray analyzer which splits secondary X-rays with a spectroscopic crystal so as to measure a wavelength and intensity of X-rays.

Figure 3A:
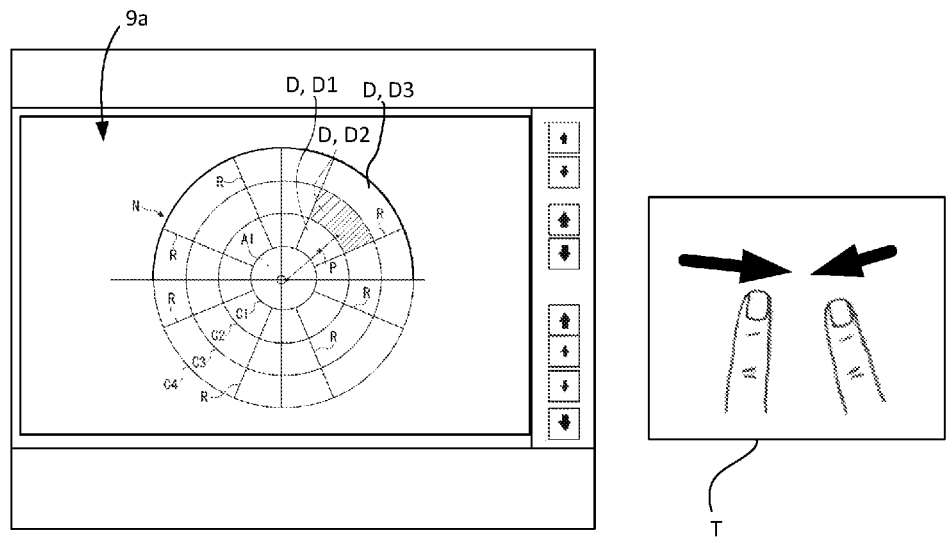
FIGS. 3A and 3B are diagrams illustrating an example of a display unit and image displayed therein according to an embodiment including a touch panel.
Figure 3B:
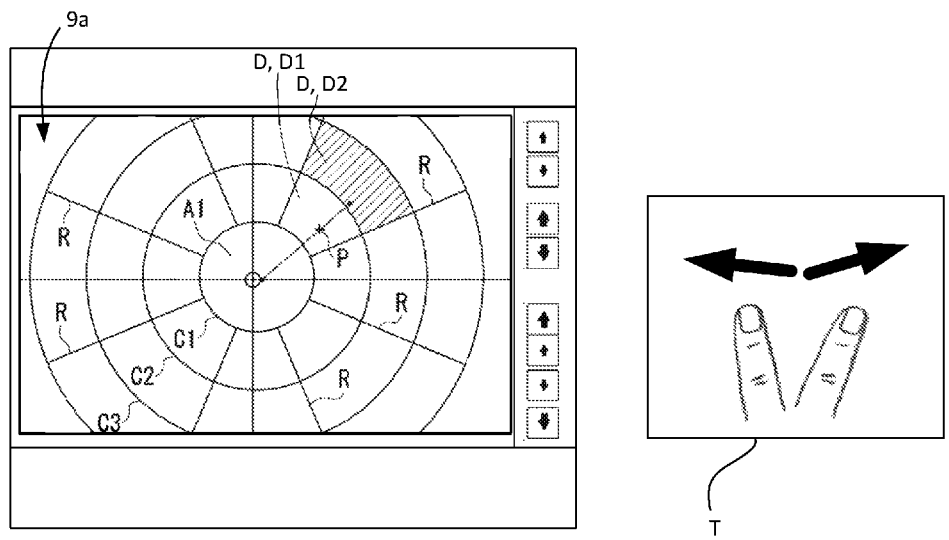

In addition, in the above-described embodiment, a mouse is used as the input unit, but, as another example, a touchpad or a touch panel (e.g., touch panel T of FIG. 1), which allows a position to be input through touching of the screen of the display unit and an input corresponding to a pinch operation including pinch-in and pinch-out to be performed, may be provided as a pointing device (input unit). Such an embodiment is illustrated in FIGS. 3A and 3B. In this case, a touch panel function is provided in the display unit, and a finger tip touching the screen of the display unit corresponds to a pointer. In addition, when a pinch operation is performed by using the touch panel, the computer in this case has a function of changing display magnification of a sample observation image captured by the observation mechanism depending on pinch-in or pinch-out. In other words, if a pinch-in operation is performed, display magnification of a sample observation image is set to be reduced (as shown in FIG. 3A), and if a pinch-out operation is performed, display magnification of the sample observation image is set to be increased (as shown in FIG. 3B).

As described above, in another example described above, when a pinch operation is performed by using the touch panel, the computer has a function of changing display magnification of a sample observation image captured by the observation mechanism depending on pinch-in or pinch-out, and thus a magnification changing button of the toolbar or the like is not required to be pressed, and thus operability can be further improved.

In addition, the touch panel may be used as the input unit in the same manner as a mouse. For example, a drag-and-drop operation is performed with finger tips, and thus the sample stage can be moved by the position adjustment mechanism in the same manner as in the above-described method. Therefore, even in an operation on the touch panel using finger tips which do not have high positioning accuracy, an operation related to the sample stage can be intuitively performed.

What is claimed is:

1. A fluorescent X-ray analyzer comprising:
   a sample stage on which a sample is placed;
   an X-ray source configured to irradiate the sample with primary X-rays;
   a detector configured to detect secondary X-rays generated from the sample irradiated with the primary X-rays;
   a position adjustment mechanism configured to adjust relative positions of the sample stage and the primary X-rays;
   an observation mechanism for obtaining an observation image of the sample on the sample stage; and
   a computer configured to control the position adjustment mechanism, wherein the computer comprises:
      a display unit that displays the sample observation image on an observation screen; and
      an input unit for inputting a position on a screen of the display unit with a pointer and for performing a drag-and-drop operation, the input unit including at least one input element configured to change between a held state and a released state,
   wherein the computer has a function of, in response to the pointer being moved from inside a central region of the observation screen to a certain position outside of the central region by the input unit being dragged while maintaining the at least one input element in the held state, driving the position adjustment mechanism in a movement direction and at a movement speed corresponding to a direction and a distance of the certain position relative to the central region, so as to move the sample stage,
   wherein the sample stage is driven to move at a first speed when the distance of the certain position relative to the central region is a first distance, and
   wherein the sample stage is driven to move at a second speed, greater than the first speed, when the distance of the certain position relative to the central region is a second distance greater than the first distance.

2. The fluorescent X-ray analyzer according to claim 1, wherein the computer is configured to control the display unit to display, on the observation screen, mesh lines that are formed by a plurality of concentric lines, which diameters are set to become larger in stages, and a plurality of radial division lines which extend from the minimum concentric line with a minimum diameter to the maximum concentric line with a maximum diameter in a radial form among the concentric lines, the observation screen being partitioned into a plurality of division regions with the mesh lines, and
wherein the central region is located inside of the minimum concentric line, and the certain position corresponds to one of the plurality of division regions.

3. The fluorescent X-ray analyzer according to claim 1, wherein the input unit is a mouse for controlling the pointer on the screen of the display unit, the mouse having a rotatable wheel and allowing an input corresponding to a rotation operation of the wheel to be performed, and
wherein the computer has a function of changing display magnification of the sample observation image captured by the observation mechanism in accordance with a rotation direction of the wheel in response to the wheel being rotated.

4. The fluorescent X-ray analyzer according to claim 1, wherein the input unit is a touch panel which allows a position to be input through touching of the screen of the display unit, the touch panel allowing an input corresponding to pinch operations including pinch-in and pinch-out to be performed, and
wherein the computer has a function of changing display magnification of the sample observation image captured by the observation mechanism depending on the pinch-in or the pinch-out in response to receiving the pinch operation through the touch panel.

* * * * *